United States Patent [19]

Normann

[11] 4,015,590
[45] Apr. 5, 1977

[54] BALLOON ACTIVATED BLOOD PUMP

[75] Inventor: Nils A. Normann, Houston, Tex.

[73] Assignee: Baylor College of Medicine, Houston, Tex.

[22] Filed: Apr. 12, 1976

[21] Appl. No.: 675,848

[52] U.S. Cl. .................... 128/1 D; 128/DIG. 3; 3/1.4; 417/389

[51] Int. Cl.[2] .......................... A61B 19/00

[58] Field of Search .............. 128/1 D, 1 R, 214 R, 128/274, 349 B; 3/1.4; 417/474, 475, 389

[56] References Cited

UNITED STATES PATENTS

| 3,504,662 | 4/1970 | Jones | 128/1 D |
|---|---|---|---|
| 3,692,018 | 9/1972 | Goetz et al. | 128/1 D |
| 3,769,960 | 11/1963 | Robinson | 128/1 D |
| 3,885,251 | 5/1975 | Pedroso | 3/1.7 X |
| 3,939,820 | 2/1976 | Grayzel | 128/1 D |

FOREIGN PATENTS OR APPLICATIONS

| 2,340,755 | 2/1975 | Germany | 128/1 D |

Primary Examiner—Stephen C. Pellegrino

[57] ABSTRACT

A pneumatically driven balloon activated blood pump for connection either in parallel with or to one side of the heart for temporary mechanical support of an inadequately functioning heart. A tubular conduit with a sealable opening for insertion or removal of the balloon having an inlet and an outlet for connection to the circulatory system. A gas line extends from outside of the conduit through the opening and into the conduit and is connected to an inflatable balloon which is expanded and contracted by gas to form the blood propelling member. An inlet and an outlet valve are positioned on opposite sides of the balloon to provide unidirectional flow of blood through the pump. The inlet valve may be a separate occluder balloon connected to and actuated from the gas line or may be a portion of the balloon occluding the inlet side of the conduit during inflation. An outlet valve may be attached to the pump balloon. The inflatable balloon and valves may be insertable and removable through one or more sealable openings.

14 Claims, 5 Drawing Figures

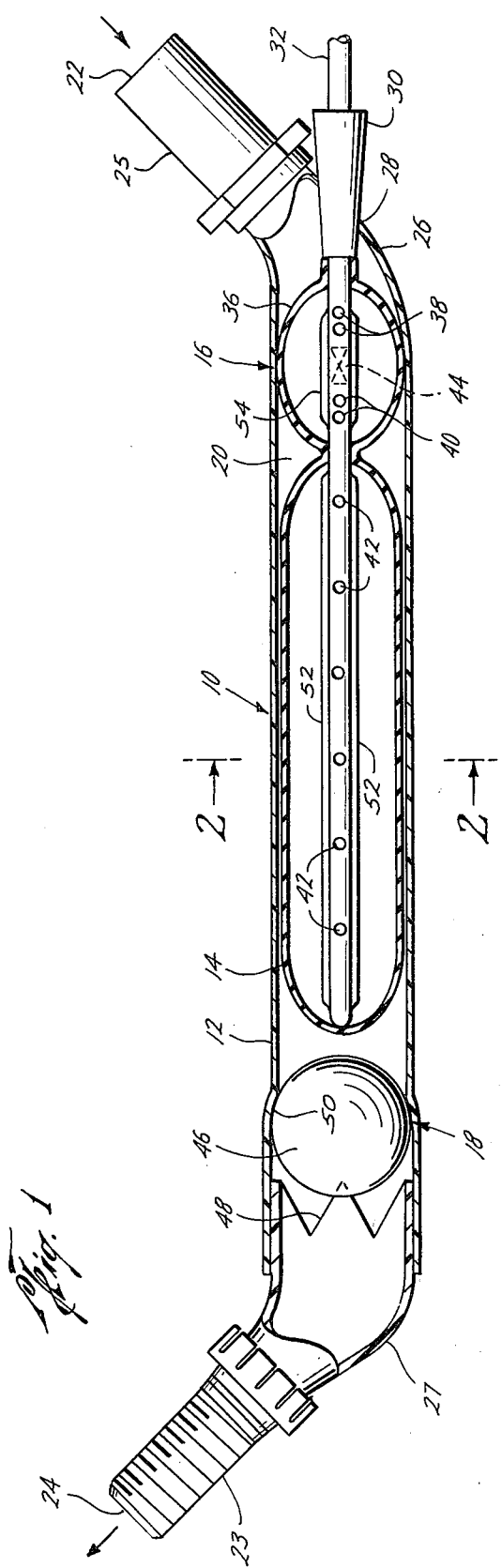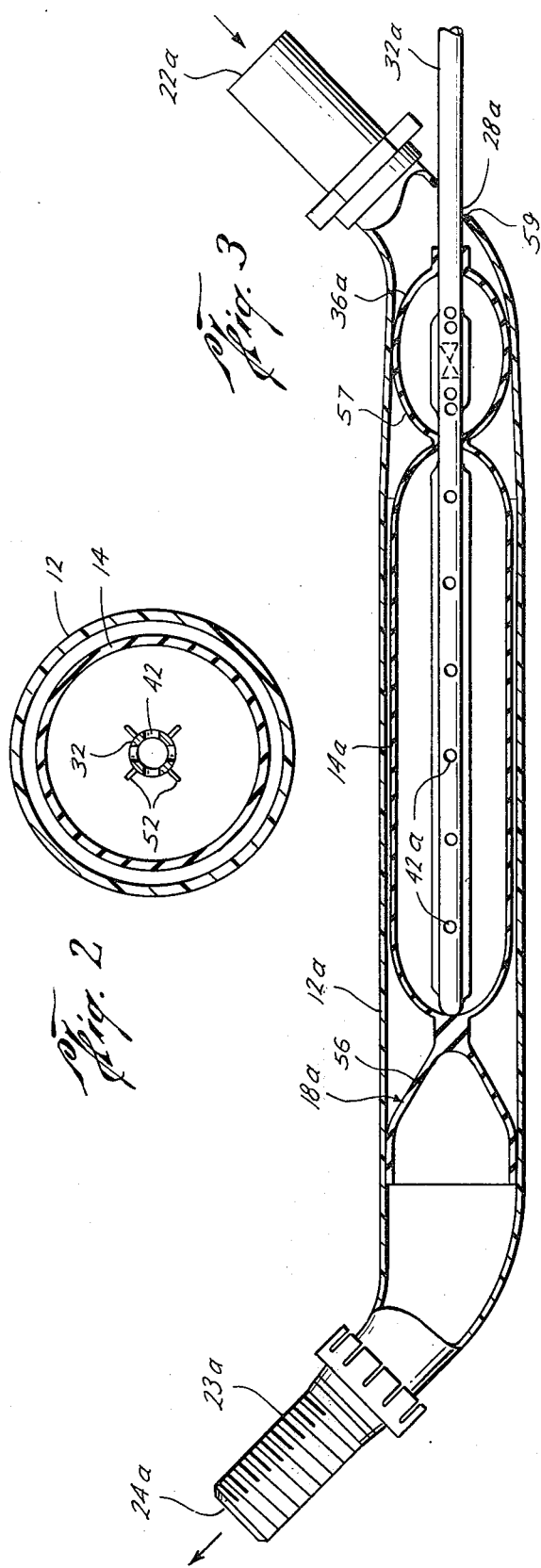

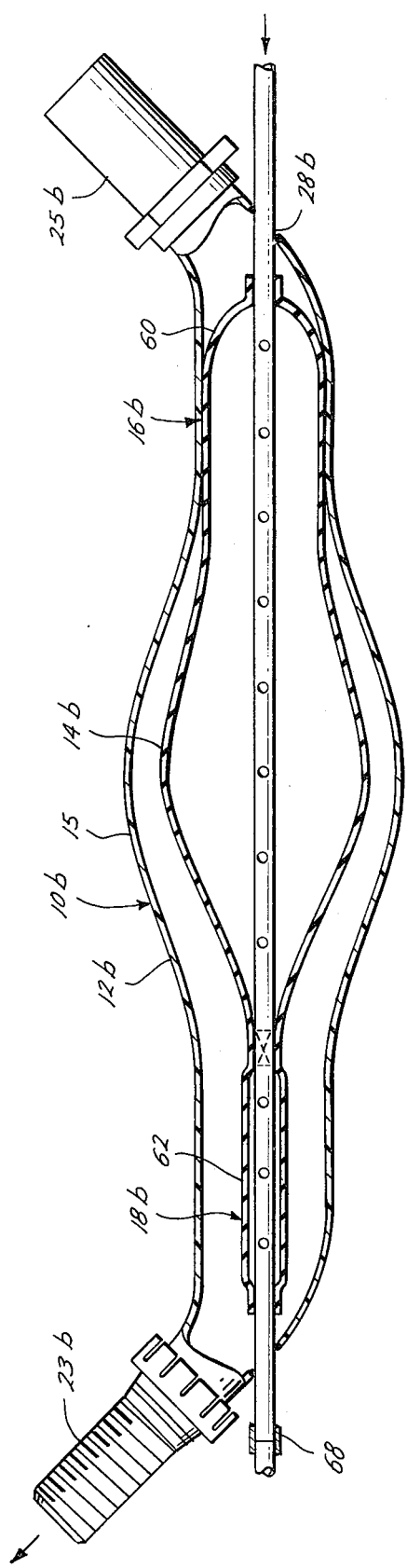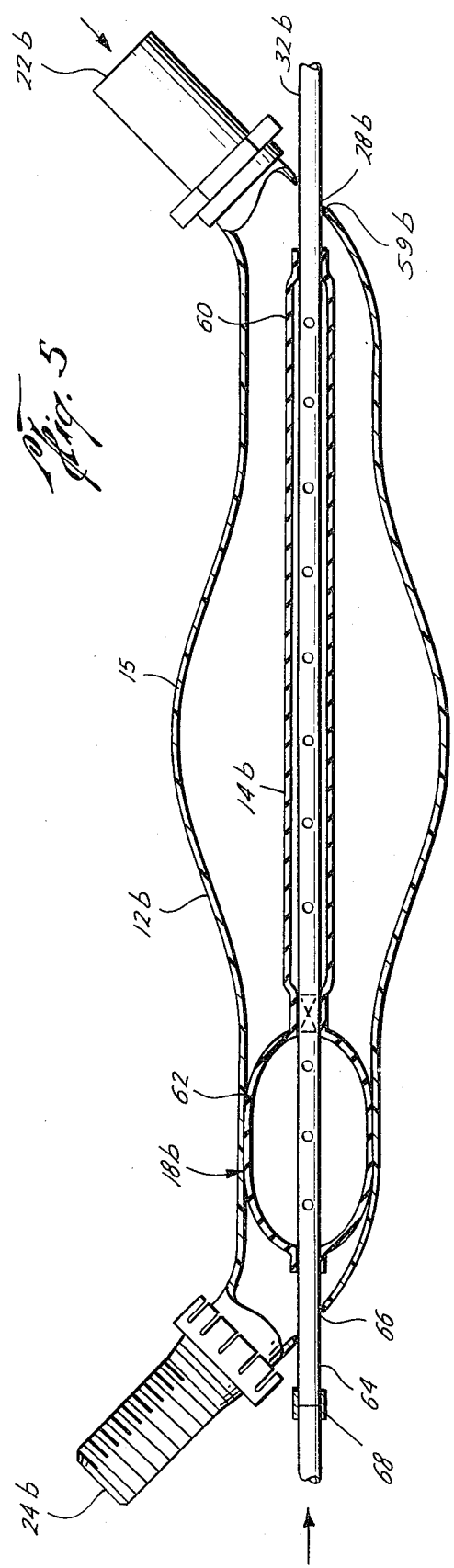

4,015,590

BALLOON ACTIVATED BLOOD PUMP

BACKGROUND OF THE INVENTION

The invention described herein was made in the course of work under a grant or award from the Department of Health, Education, and Welfare.

Presently, there are in use pulsatile, circulatory blood pumps which are pneumatically operated, having blood and gas containing compartments separated either by a diaphragm or by incorporating within a rigid housing, a blood containing bladder. Pulses of pressurized gas cause unidirection flow by means of inflow and outflow valves. However, these pumps are relatively complex. The valves are likely to cause thrombus problems, bladder compression is critical, a closed system pneumatic drive is necessary to avoid overcollapse of the bladder, the flexing member cannot be replaced during use without replacing the whole pump, and the pump is expensive.

The present invention is directed to an improved, but simplified, pulsatile blood pump using a clinically accepted nonthrombogenic balloon, such as shown in U.S. Pat. No. 3,692,018, which is placed in a tubular housing with unidirectional inlet and outlet valves and which has the following advantages:

1. structural and flow dynamic simplicity, including valve arrangements;
2. nonthrombogenic balloons are commercially available;
3. blood-contacting surfaces can be coated with or made of hemocompatible materials;
4. the use of a pneumatic balloon avoids the problem of "overcollapse";
5. the flexing member, that is, the balloon and the valves, if desired, are replaceable—while the pump is still connected to the patient;
6. the pump can be operated by the use of existing drive systems;
7. unitized construction of pump housing and connecting blood conduits is possible;
8. the capacitance method for on-line pump monitoring as described in patent application Ser. No. 618,718, filed Oct. 1, 1975, entitled Remote Electrical Monitoring of Gas Activated Blood Pumps, plus closed-loop control of pump timing and stroke volume, can be employed;
9. relative simplicitiy in design and fabrication should result in a less costly product.

SUMMARY

The present invention is directed to a nonthrombogenic, pulsatile heart pump for temporary, paracorporeal circulatory support, for instance after cardiac surgery. The present pump utilizes simple flow dynamics to avoid turbulence and stasis of the blood and utilizes an inflatable balloon as the blood propelling member.

A further object of the present invention is the provision of a bypass blood pump having a rigid or semi-rigid tubular conduit housing with a sealable opening in the housing through which a gas line may extend for actuating the balloon and permits easy installation and removal of the balloon, even while the pump is connected to the patient.

A still further object of the present invention is the provision of an inlet and an outlet valve positioned on opposite sides of the balloon to provide unidirectional blood flow. The inlet and outlet valves may be part of the pumping balloon or a separate occluder balloon connected to and actuated from a gas line. In addition, the valves can be connected to the balloon whereby both valves as well as the balloon may be inserted and removed through a sealable opening.

Still a further object is the provision of supporting the balloon from the gas line in which the gas line includes a plurality of openings for communicating gas between the interior of the balloon and the interior of the line and in which the exterior of the gas line includes ribs for preventing the balloon from collapsing on and closing the line openings.

A further object is the provision of an elastic nonfolding balloon positioned in an enlarged cross-sectional area of the conduit and extending out of the enlarged area to act both as a pumping member and an inlet valve.

Yet still a further object of the present invention is the provision of making the tubular housing, the balloon and the gas line of a straight or a curved shape thus providing an optimum configuration for coacting with the human body.

Other and further objects, features and advantages will be readily apparent from the following description of a presently preferred embodiment of the invention given for the purpose of disclosure and taken in conjunction with the accompanying drawings.

BRIEF DESCRIPTION OF THE DRAWINGS

FIG. 1 is an elevational view, illustrating the apparatus of the present invention, FIG. 2 is a cross-sectional view taken along the line 2—2 of FIG. 1, FIG. 3 is an elevational view of a modification of the present invention, FIG. 4 is an elevational view of a further modification of the present invention shown in the output cycle, and FIG. 5 is an elevational view of the apparatus of FIG. 4 shown in the input cycle.

DESCRIPTION OF THE PREFERRED EMBODIMENT

Referring now to the drawings, and particularly to FIG. 1, the pulsatile blood pump of the present invention is generally indicated by the reference numeral 10, and generally includes a housing 12, a pneumatically driven pump balloon 14, an inflow valve 16, and an outflow valve 18.

The housing 12 includes a straight or curved tubular conduit having a generally smooth, continuous and uniform passageway 20 therein which advantageously provides for a smooth flow of blood with a minimum of turbulence. It is important that turbulence should be avoided as this tends to damage blood components and also induces undesired clotting of the blood. The housing 12 includes a suitable inlet 22 and an outlet 24 having suitable connections 23 and 25, respectively, for conventionally connecting the pump to the circulatory system of the body. Usually the pump is connected in parallel with the heart or left side of the heart for providing a temporary, mechanical pump support for an inadequately functioning heart. For example, and typically, the pump 10 may be used as an intracorporal or as a paracorporal left ventricular bypass pump in left ventricular failure in conjunction with cardiac surgery by connecting the input 22 to the left atrium or the left ventricle and the outlet 24 to the aorta or a systemic artery. Preferably, the tubular conduit 12 is of any suitable rigid or semi-rigid optically clear thermoplastic material which may be heat treated, if desired, and may be curved so that the inlet 22 and outlet 24 provide convenient connections with the circulatory system and any suitable material, such as polyvinyl chloride or a material sold under the trademark "Tygon" is satisfactory. The inside diameter of the conduit 12 is larger than the diameter of the inflated balloon 14 and in one satisfactory pump the inside diameter of the housing 12 was 5 mm. larger than the diameter of the inflated balloon 14.

Preferably, the housing or tubular conduit 12 includes a gradual taper of diameter and smooth bends 26 and 27 for providing smooth blood flow and convenient attachments. The bend 26, positioned between the inlet 22 and the balloon 14, has a sealable opening 28 on the outside of the curve 26, such as may be provided by an elastic polyurthane sleeve 30 forming a channel through the wall of the housing 12 for a gas line 32 which extends from the outside of the housing 12 and into the passage 20. The sleeve 30 serves both as an insertion channel and as a seal around the gas line 32.

The pump balloon 14 is connected to the gas line 32 and is gas driven and serves as the flexing, blood propelling member. Balloons, made of blood-compatible polyurethane, are already clinically accepted for use in cardiac assist. Contrary to the conventional design of bypass blood pumps, in which the inside of a bladder constitutes the blood containing compartment, the blood in the present pump 10 is contained between the balloon 14 and the inside of the housing wall 12. Consequently, the housing 12 and balloon 14 form a uniform continuous, tubular blood flow conduit, thereby reducing turbulence. The present pump 10 also avoids overcollapse since the inflated balloon 14 will not expand beyond a given size. Therefore, the present pump 10 avoids the problem of overcollapse present in conventional pumps wherein the compression of a blood containing bladder may cause the internal bladder surfaces to be pressed together, which hemocompatibility-wise, is an undesirable occurrence. In addition, since the balloon 14 is connected to and supported from the gas line 32, the balloon 14 may be inserted and removed through the sleeve 30, even while the pump 10 is still connected to the patient and the position of the insertion sleeve 30 on the outside of the curved portion 26 of the housing 12 provides an appropriate angle for the insertion and removal of the balloon 14. Furthermore, in the event that the housing 12 is curved, the polyurethane balloon 14 can be given an axial curvature by means of appropriate heat treatment.

Unidirectional flow through the pump 10 from the inlet 22 to the outlet 24 is achieved by utilizing the inlet valve 16 and the outlet valve 18, which may be of any suitable clinical prosthetic type and may be placed anywhere in the conduit 12 between the pump balloon 14 and the connections to the circulatory system. In the embodiment of FIG. 1, the inlet valve 16 includes an occluder balloon 36 which in its inflated state has the same outside diameter as the inside diameter of the housing 12. The occluder balloon 36 is smoothly tapered and is connected to the gas line 32. The gas line 32 includes one or more openings 38 which serve to communicate any suitable gas, such as carbon dioxide or air between the inside of the gas line 32 and the inside of the occluder balloon 36. The gas line 32 also includes openings 40 which serve as a communication path between the inside of the gas line 32 and the inside of the occluder balloon 36 and further includes openings 42 which serve to communicate gas between the inside of the gas line 32 and the pump balloon 14. An obstruction 44 is provided in the air line 32 between the openings 38 and 40 which forces gas being supplied by the line 32 to pass through the occluder balloon 36 before entering the pump balloon 14. Thus, the occluder balloon 36 will inflate ahead of the balloon 14 at the beginning of pump systole and, similarly, deflate first at the beginning of the pump diastole to provide the desired one-way valve action of valve 16. Commercially available drive systems such as Avco Model IABP-7 may be connected to the gas line 32 for actuating the pump 10.

The outlet check valve 18 may consist of a simple hemocompatible carbon ball 46, such as sold under the trademark "Pyrolite", located within a portion of the housing 12 or preferably in a downstream conduit joint. Notches in the downstream portion of the joint provide a cage 48 and the upstream portion provides a close-off ball seat 50. When the pump balloon 14 contracts, the ball 46 seats against the seat 50 to close the valve 18 and when the balloon expands, the ball 46 moves to the cage 48 opening the outlet valve 18.

In order to prevent blockage of the gas openings 38, 40 and 42 on collapse of the occluder balloon 36 and pump balloon 14, ribs may be provided on the exterior of the gas line 32 to insure that the gas openings remain open at all times. As shown in FIG. 2, ribs 52 are provided on the exterior of the gas line 32 between the openings 42 preventing blockage of the openings 42. Similarly, ribs 54 are provided inside of the occluder balloon 36 for the same purpose.

Since one of the problems with blood pumps is the clotting of the blood, it is necessary that the materials used in the pump be compatible with the blood. Therefore, the pump elements exposed to the blood may be made of any suitable blood compatible material such as special polyurethanes or can be coated with such materials.

In use, with the pump balloon 14 and the occluder balloon 16 in the collapsed condition, blood will fill the passageway 20 in the housing 12 surrounding the pump balloon 14. As gas is supplied to the gas line 32 from a drive system, gas will flow through the openings 38 into the occluder balloon 36 expanding the occluder balloon 36 until it contacts the interior of the housing 12 thereby closing the inlet valve 16. As a supply of gas through the line 32 continues, gas flows through the openings 40 and out the openings 42 to expand the pump balloon 14 to force the blood in the passageway 20 through the outlet valve 18. At the conclusion of the output cycle, gas is withdrawn from the gas line 32 causing sequential collapse of the occluder balloon 16 and the pump balloon 14 and closing the outlet valve 18. The contraction of the balloon 36 again opens the inlet valve 16 and contraction of balloon 14 draws in blood through the inlet 22 to the passageway 20.

Other and further modifications of the present invention can be made in which like parts corresponding to FIG. 1 are similarly numbered with the suffixes *a* and *b*.

In the embodiment shown in FIG. 3, the expanded diameters of the occluder balloon 36*a*, and pump balloon 14*a* are the same for the convenience of manufacture. However, in order for the occluder balloon 36*a* to contact the interior wall of the housing 12*a* to form a check valve, the housing 12a is tapered inwardly at 54 so as to coact with the occluder balloon 36a when it is in the expanded position to act as the inlet valve. Additionally, in order to improve the flow dynamics, the opening 28a is formed in an elastic membrane 54 in place of the sleeve 30 shown in FIG. 1. In addition, a different type of outlet valve 18a may be provided such as a flexible outwardly expanded umbrella 56 which is connected to the gas line 32a. The outlet valve 18a will fold inwardly during ejection to allow blood to flow through the outlet 24a, but will expand against the interior of the conduit wall 12a during pump diastole. In addition, since the valve 18a is connected to the gas line 32a it is also removable from and insertable through the opening 28a for ease of replacement.

Referring now to the embodiment shown in FIGS. 4 and 5, the pumping balloon 14b is preferably an elastic, nonfolding balloon which acts both as the blood propelling member and the inlet valve 16b. The conduit 12b includes an enlarged section 15 positioned about the pumping portion of the balloon 14b while the balloon portion 60, which acts as the inlet valve 16b, extends out of the enlarged conduit section 15 and into a smaller section. Therefore, when gas is transmitted through gas line 32b, the balloon 14b will expand outwardly, but the portion 60 will occlude the conduit 12b and act as a closed inlet valve. Continued expansion of the balloon 14b will pump the blood downstream of the inlet valve 16b. The elastic balloon 14b will contract on reducing the gas pressure to the cylindrical shape shown in FIG. 5. Another advantage of balloon 14b is that the intermittent expansion of an elastic, nonfolding balloon may be less prone to clot formation.

While any suitable outlet valve 18b may be used with the embodiment of FIGS. 4 and 5, an outlet occluder balloon 62 is shown which may be, as with any of the outlet valves, positioned anywhere in the conduit 12b between the balloon 14b and the connection to the circulatory system. The balloon 62 is here shown as connected to the pump balloon 14b, but includes a separate gas line 64 for actuation of the balloon 62 since the balloon 62 must retract, as best seen in FIG. 4 when the balloon 14b expands, and must, as best seen in FIG. 5 expand when the balloon 14b contracts. Any suitable actuation means such as a double acting piston (not shown), one side of which is connected to line 32b and the opposite side of which is connected to line 64, may be used to alternately actuate balloons 14b and 62. If the occluder balloon 62 is separate from the balloon 14b, it can be inserted and removed through the sealable opening 66. If the occluder balloon 62 is connected ot the pump balloon 14b, it may be inserted and removed with the balloon 14b through the sealable opening 28b by unfastening connection 68 in the gas line 64.

The present invention, therefore, is well adapted to carry out the objects and attain the ends and advantages mentioned as well as others inherent therein. While presently preferred embodiments of the invention have been given for the purpose of disclosure, numerous changes in the details of construction and arrangement of parts will readily suggest themselves to those skilled in the art and which are encompassed within the spirit of the invention and the scope of the appended claims.

What is claimed is:

1. A heart assist blood pump comprising,
   a tubular conduit having an inlet and an outlet for connection with the circulatory system of the body,
   a sealable opening in the conduit between the inlet and the outlet,
   a gas line extending from the outside of said conduit through the opening and into the conduit,
   an inflatable pump balloon positioned in the conduit and connected to the gas line, and the inside of the balloon in communication with the line for receiving gas from the line and inflating with positive line pressure and deflating with decreased line pressure thereby creating a pumping action in the conduit, the inflated balloon having an outside diameter smaller than the inside diameter of the portion of the conduit in which the balloon is positioned,
   an inlet valve positioned in the conduit between the balloon and the conduit inlet, and
   an outlet valve positioned in the conduit between the balloon and the conduit outlet.

2. The apparatus of claim 1 wherein the inflatable balloon is insertable and removable through the sealable opening.

3. The apparatus of claim 1 wherein the inlet and outlet valves are connected to the gas line.

4. The apparatus of claim 3 wherein the inflatable balloon, the inlet and outlet valves are insertable and removable through the sealable opening.

5. The apparatus of claim 1 wherein the gas line extends through the interior of the balloon and includes a plurality of openings for communicating gas between the interior of the balloon and the interior of the line and the exterior of the line in the balloon includes ribs for preventing the balloon from collapsing on and closing said line openings.

6. The apparatus of claim 1 wherein the inlet valve includes a second inflatable balloon connected to the gas line with its interior in communication with the interior of the gas line, and the inflated diameters of the two balloons being substantially the same, and the interior of the conduit surrounding the second balloon being smaller than the diameter of the conduit surrounding the first balloon.

7. The apparatus of claim 1 wherein the housing is a rigid or semi-rigid thermoplastic whereby the housing may be suitably shaped.

8. The apparatus of claim 1 wherein,
   the conduit includes an enlarged cross-sectional area,
   said balloon is an elastic non-folding balloon positioned in said enlarged area and extending upstream of said enlarged area whereby said balloon acts both as a pump and an inlet valve.

9. The apparatus of claim 8 wherein
   said outlet valve includes an occluder balloon connected to a second gas line, said occluder balloon connected to the pump balloon, and
   said pump balloon and occluder balloon are insertable and removable through the sealable opening.

10. The apparatus of claim 1 wherein,
    said outlet valve includes an occluder balloon connected to a second gas line extending out of the conduit through a second sealable opening.

11. The apparatus of claim 1 wherein the outlet valve is a resilient umbrella type valve and is connected to the balloon.

12. The apparatus of claim 1 wherein the outlet valve includes a joint in the conduit forming a seat and a cage, and a ball positioned therein.

13. A heart assist blood pump comprising, a tubular optically clear conduit having an inlet and an outlet for connection with the circulatory system, said conduit having a smooth passageway, said conduit having a curved portion between the inlet and the outlet and a sealable opening on the outside of the curved portion, a gas line extending from the outside of said conduit through the opening and into the conduit passageway, an inflatable balloon positioned and connected to the line, and the inside of the balloon in communication with the line for receiving gas from the line and inflating, and exhaling air to the line and deflating, the balloon thereby creating a pumping action in the passageway, an inlet valve positioned in the conduit between the balloon and the conduit inlet, and an outlet valve positioned in the conduit between the balloon and the conduit outlet.

14. The apparatus of claim 13 wherein the inlet valve is connected to the gas line, and the inlet valve and the balloon are insertable and removable through the sealable opening.

* * * * *